United States Patent [19]
Strand

[11] Patent Number: 5,454,739
[45] Date of Patent: Oct. 3, 1995

[54] ELECTRODE CONNECTOR

[75] Inventor: Jerome E. Strand, Hudson, Wis.

[73] Assignee: Minnesota Mining and Manufacturing Company, St. Paul, Minn.

[21] Appl. No.: 190,996

[22] Filed: Feb. 3, 1994

Related U.S. Application Data

[63] Continuation-in-part of Ser. No. 990,692, Dec. 15, 1992, Pat. No. 5,407,368.

[51] Int. Cl.$^6$ ...................................................... H01R 4/48
[52] U.S. Cl. ........................... 439/729; 128/639; 439/838
[58] Field of Search .................................. 439/725, 729, 439/731, 835–838; 128/639, 640, 798, 802

[56] References Cited

U.S. PATENT DOCUMENTS

| | | |
|---|---|---|
| Re. 24,906 | 12/1960 | Ulrich . |
| Re. 31,454 | 12/1983 | Hymes .................................. 128/641 |
| Re. 33,353 | 9/1990 | Heinecke .............................. 428/40 |
| D. 244,879 | 6/1977 | Manno ................................. D24/29 |
| D. 328,283 | 7/1992 | Strand ................................. D13/149 |
| 3,090,029 | 5/1963 | Stroebel . |
| 3,389,827 | 6/1968 | Abere et al. . |
| 3,641,473 | 2/1972 | Attaway . |
| 3,644,877 | 2/1972 | Carbonneau . |
| 3,976,055 | 8/1976 | Monter et al. ................. 128/2.06 E |
| 4,061,408 | 12/1977 | Bast et al. . |
| 4,112,213 | 9/1978 | Waldman ............................. 526/279 |
| 4,166,465 | 9/1979 | Esty et al. ....................... 128/303.13 |
| 4,178,052 | 12/1979 | Ekbom et al. . |
| 4,310,509 | 1/1982 | Berglund et al. ................... 424/28 |
| 4,323,557 | 4/1982 | Rosso et al. ......................... 424/28 |
| 4,391,278 | 7/1983 | Cahalan et al. .................... 128/640 |
| 4,539,996 | 9/1985 | Engel ................................. 128/640 |
| 4,543,958 | 10/1985 | Cartmell ............................. 128/640 |
| 4,554,924 | 11/1985 | Engel ................................. 128/640 |
| 4,555,155 | 11/1985 | Drake . |
| 4,640,563 | 2/1987 | LeBlanc . |
| 4,657,023 | 4/1987 | Kuhn ................................. 128/640 |
| 4,679,563 | 7/1987 | Wada et al. ........................ 128/640 |
| 4,694,835 | 9/1987 | Strand ................................ 128/640 |
| 4,700,997 | 10/1987 | Strand ................................ 439/372 |
| 4,702,256 | 10/1987 | Robinson et al. .................. 128/639 |
| 4,732,808 | 3/1988 | Krampe et al. .................... 428/355 |
| 4,795,516 | 1/1989 | Strand ................................ 156/235 |

(List continued on next page.)

FOREIGN PATENT DOCUMENTS

| | | |
|---|---|---|
| 0051935 | 5/1982 | European Pat. Off. . |
| 0210020 | 1/1987 | European Pat. Off. . |
| 0510786 | 10/1992 | European Pat. Off. . |
| 3307896 | 9/1984 | Germany . |
| 0648067 | 12/1950 | United Kingdom . |
| 1519782 | 8/1978 | United Kingdom . |
| PCT/WO90/ 01224 | 2/1990 | WIPO . |

OTHER PUBLICATIONS

"Human Factors Design Handbook", Information and Guidelines for the Design of Systems, Facilities, Equipment, and Products for Human Use, Wesley E. Woodson, (3 pages).
"Melinex Technical Data", ICI Americas Inc., Form No. 5773h(C), dated Dec., 1986 (5 pages).
German Geschmacksmuster M 9304825.4.
A three (3) page document from Cardio Connector Corporation regarding ASTRO–TRACE™.

Primary Examiner—Khiem Nguyen
Attorney, Agent, or Firm—Gary L. Griswold; Walter N. Kirn; Jeffrey J. Hohenshell

[57] ABSTRACT

A connector for use with a tab style biomedical electrode as disclosed. The connector comprises pivotally mounted movable and fixed jaws and a spring biasing the jaws toward a closed position. The connector is readily assembled, while retaining a secure connection between the jaws. Preferred embodiments achieve a high tab release force and yet provides an acceptably low actuation force. Preferably, the fixed jaw includes a smooth, continuous surface which facilitates insertion of the tab between the jaws of the connector.

20 Claims, 9 Drawing Sheets

U.S. PATENT DOCUMENTS

| | | | |
|---|---|---|---|
| 4,797,125 | 1/1989 | Malana | 439/729 |
| 4,798,208 | 1/1989 | Faasse, Jr. | 128/640 |
| 4,798,642 | 1/1989 | Craighead et al. | 156/252 |
| 4,842,558 | 6/1989 | Strand | 439/863 |
| 4,848,353 | 7/1989 | Engel | 128/640 |
| 4,852,571 | 8/1989 | Gadsby et al. | 128/640 |
| 4,893,626 | 1/1990 | Henley et al. | 128/640 |
| 4,915,656 | 4/1990 | Alferness | 439/729 |
| 4,917,928 | 4/1990 | Heinecke | 428/41 |
| 4,917,929 | 4/1990 | Heinecke | 428/41 |
| 4,922,911 | 5/1990 | Wada et al. | 128/640 |
| 4,952,177 | 8/1990 | Drake et al. | 439/828 |
| 5,012,810 | 8/1991 | Strand et al. | 128/640 |
| 5,058,589 | 10/1991 | Ding et al. | 128/640 |
| 5,078,138 | 1/1992 | Strand et al. | 128/640 |
| 5,079,139 | 1/1992 | Strand et al. | 128/640 |
| 5,133,355 | 7/1992 | Strand et al. | 128/640 |
| 5,137,475 | 8/1992 | Olms | 439/725 |
| 5,178,144 | 1/1993 | Cartmell | 128/640 |
| 5,195,523 | 3/1993 | Cartmell et al. | 128/640 |
| 5,209,679 | 5/1993 | Quinlan | 439/822 |
| 5,295,872 | 3/1994 | Christensson | 439/822 |

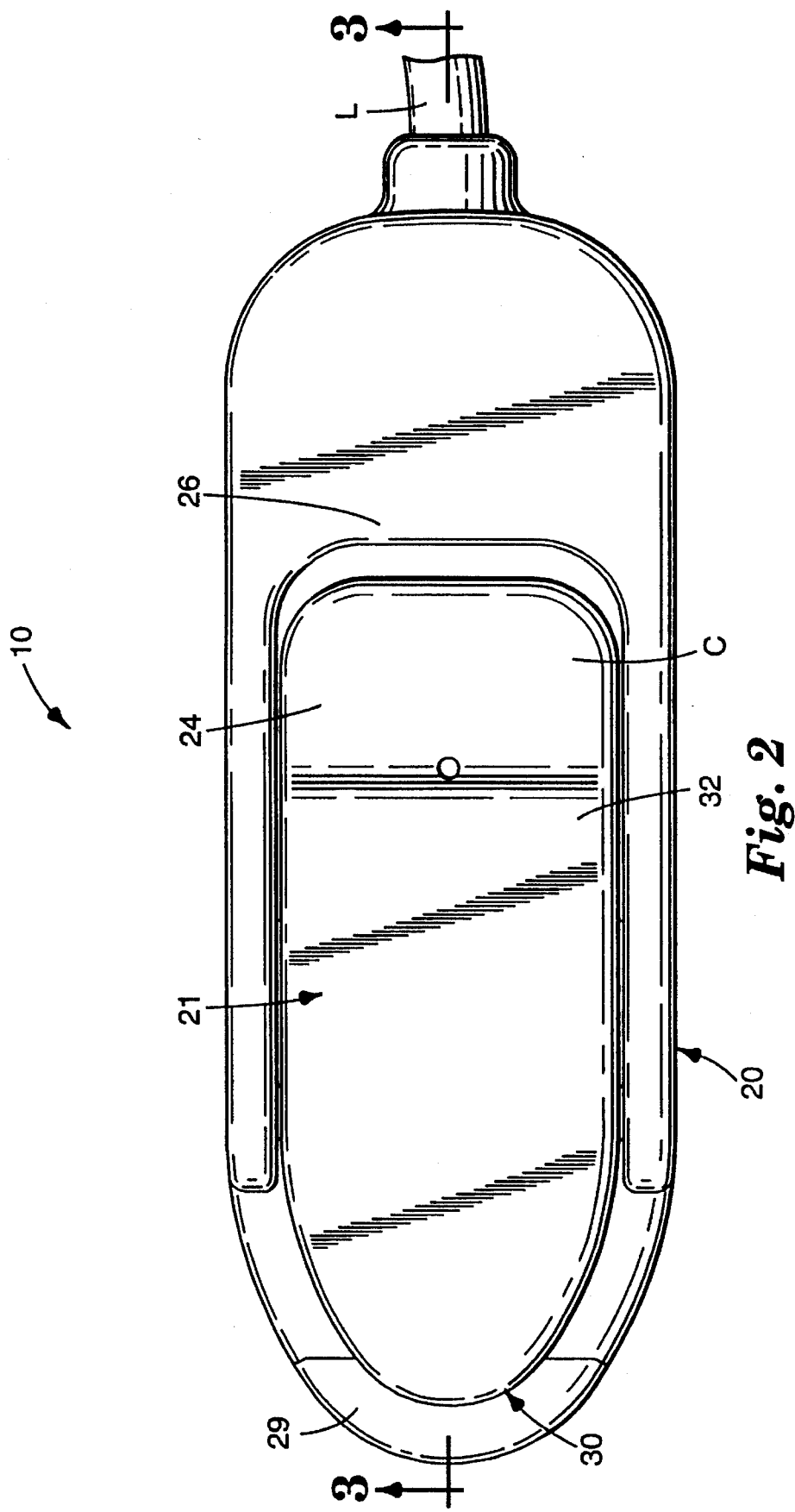

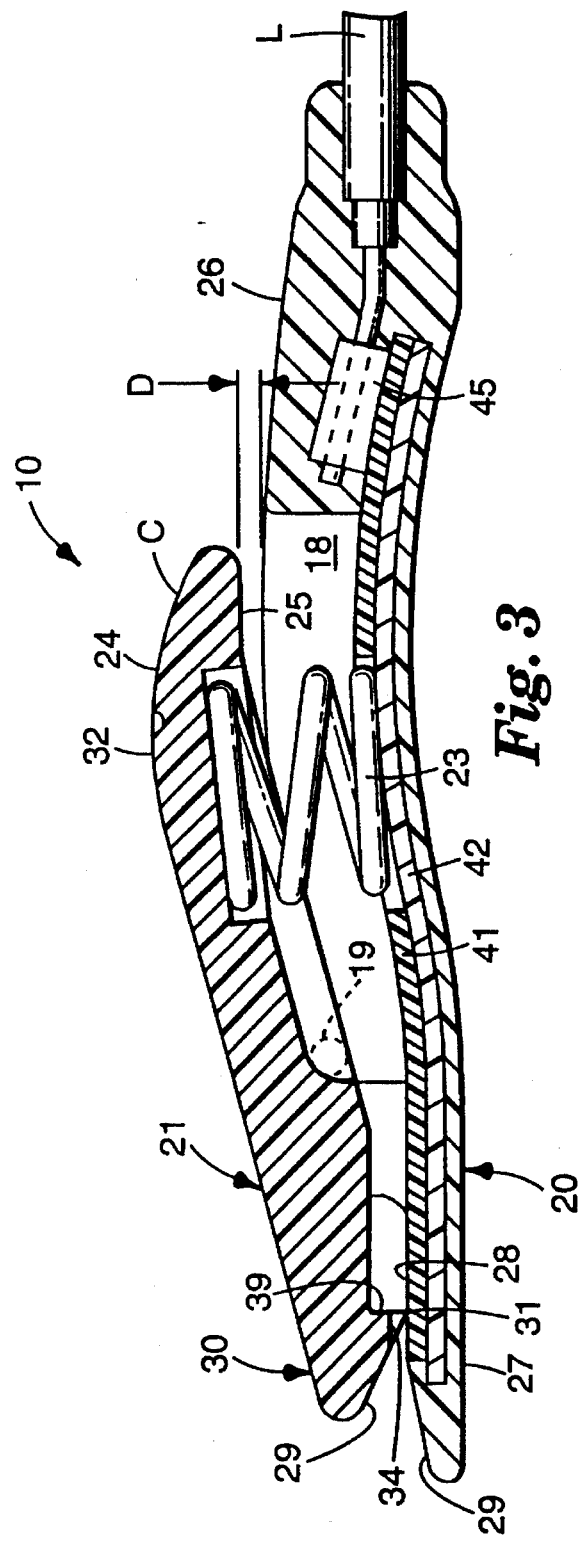
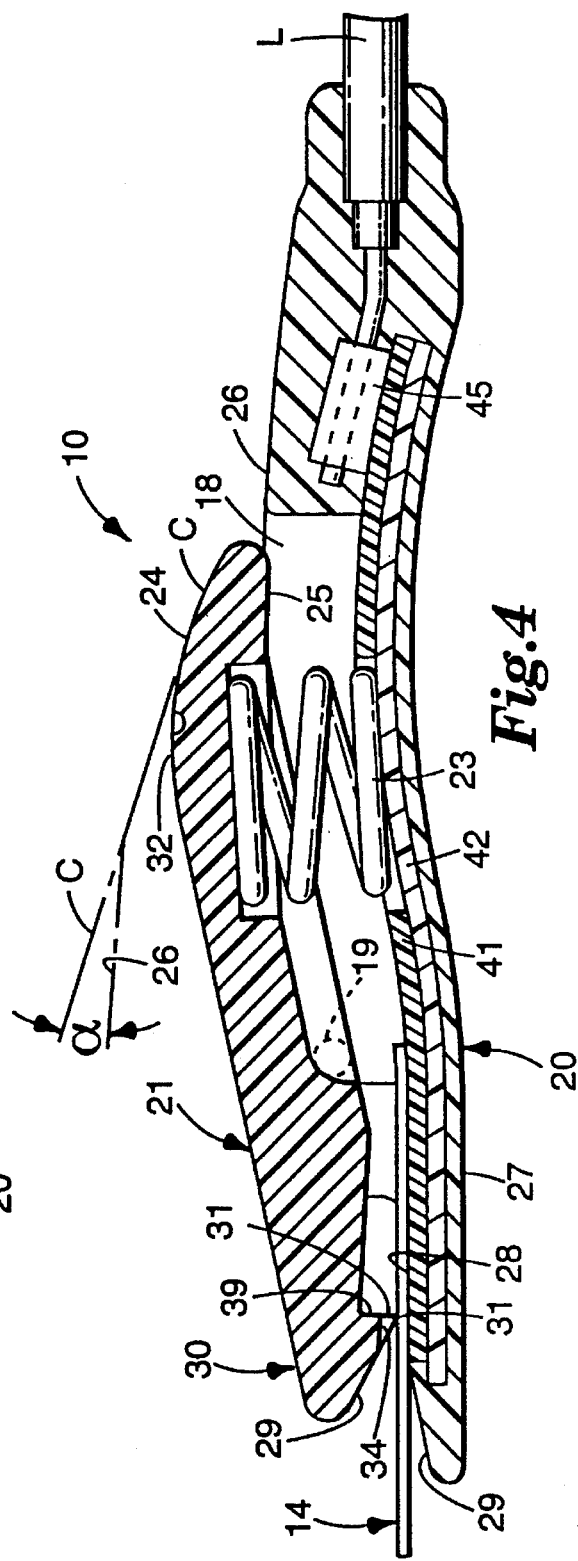
Fig. 3
Fig. 4

ELECTRODE CONNECTOR

This application is a continuation-in-part of U.S. patent application Ser. No. 07/990,692 filed Dec. 15, 1992 now U.S. Pat. No. 5,407,368 (naming Jerome E. Strand and Perry S. Dotterman as joint inventors) the contents of which are herein expressly incorporated by reference.

THE FIELD OF INVENTION

The present invention relates to connectors for biomedical electrodes having an electrically conductive contacting tab with generally flat upper and lower surfaces.

BACKGROUND

The art is replete with different types of biomedical electrodes which have an electrically conductive contacting tab. Examples of such biomedical electrodes are described in U.S. Pat. Nos. 4,543,958 to Cartmel, 4,798,208 to Faasse, Jr., 5,012,810 to Strand et al., 5,078,138 to Strand et al., 5,078,139 to Strand et al., 5,133,356 to Bryan et al., and 5,215,087 to Anderson, the entire contents of each of which are herein expressly incorporated by reference. Particular examples of such electrodes include 3M Red Dot™ ECG and EKG electrodes generally available from the Minnesota Mining and Manufacturing Co. (3M) of St. Paul., Minn. Typically, such electrodes have a substantially flat construction which leads to significant advantages including: (1) such an electrode is less conspicuous when worn under a patient's clothes and less obstructive to other medical procedures, and (2) the low profile of tab-style electrodes provides a structure which is free of any substantial projections that might cause discomfort for a patient should the patient be bumped in the vicinity of the electrode or should the patient lie on he electrode.

The art is also replete with connectors for electrically connecting medical equipment to a tab-style electrode. For example such medical equipment may comprise electrical signal receiving instrumentation, diagnostic equipment, stress monitoring equipment or other testing equipment for detecting a patient's electrical signals. Other examples of medical equipment include therapeutic electrical instrumentation such as transcutaneous electronic nerve stimulation (TENS) devices used for pain management and neuromuscular stimulation (NMS) equipment used for treating conditions such as scoliosis. Medical equipment may also include the equipment used in electrosurgery or equipment used with defibrillation pads for emergency cardiac treatment.

Examples of connectors for connecting medical equipment to a tab-style biomedical electrode include U.S. Pat. Nos. 4,061,408 to Bast et al., 4,555,155 to Drake, 4,700,997 to Strand, 4,842,558 to Strand, and 4,952,177 to Drake et al.

The art also includes "alligator" type electrical connectors. An "alligator" type electrical connector typically includes a fixed jaw and a movable jaw, a pin for mounting the movable jaw for pivotal movement relative to the fixed jaw between tab accept and closed positions and a spring for biasing the movable jaw toward the closed position. A leadwire is typically fixedly connected to the fixed jaw so that the fixed jaw does not move relative to the leadwire. As used herein, the term "fixed jaw" when used to describe one of the jaws of an "alligator" type connector, means that jaw which remains stationary or fixed relative to the leadwire when the connector is opened. Particular examples of "alligator" type electrical connectors include U.S. Pat. Nos. 3,090,029 to Stroebel, 3,644,877 to Carbonneau, 4,797,125 to Malana, 4,702,256 to Robinson et al., and 5,058,589 to Ding et al.

Prior art "alligator" type electrical connectors suffer from many drawbacks. In order to ensure a very high pull off force of the connector from the tab, some prior art "alligator" type electrical connectors include a very strong spring which renders the electrical connector difficult to open. Also, some prior art electrical connectors include a hole, depression, groove, slot, slit or other discontinuous surface in a jaw which is designed to deflect the tab of the electrode. Such deflection of the tab generally results in a higher grasping force for the tab but also tends to mar, puncture or otherwise damage the conductive surface of the electrically conductive contacting tab of the biomedical electrode. Such damage may potentially result in a loss of continuity or may otherwise adversely affect the electrical properties of the biomedical electrode.

Some jaws of prior art "alligator" electrical connectors include teeth, abutment surfaces, labyrinth-like or tortuous paths or an otherwise rough surfaces. A rough surface may include a structure that substantially deforms or deflects the electrode contacting tab during insertion of the tab into the connector. Again, the deflection of the tab into a surface irregularity may increase the tab pull off force of the connector, but not without costs. The rough surface may "catch" the electrically contacting tab and cause the contacting tab to bend or otherwise deform while the tab is being inserted into the connector. Such action may render the electrical connector difficult to place on the tab of an electrode.

Also, the V-shaped nature of many prior art "alligator" type connectors render them particularly susceptible to tangling with the leadwires of other leadwires and connectors as the leadwire of one assembly may easily slip between proximal ends of the fixed and movable jaws of another assembly.

Some existing prior art "alligator" type electrical connectors may be unsuitable for biomedical use as they have relatively sharp portions which may be uncomfortable for some patients. For example, should the patient roll on top of the connector, a sharp edge or tooth may cause discomfort for the patient.

Finally, U.S. patent application Ser. No. 07/990,692 filed Dec. 15, 1992 (naming Jerome E. Strand and Perry S. Dotterman as joint inventors) discloses an electrode connector comprising pivotally mounted fixed and movable jaws that are spring biased to a closed position. The jaws of that connector are mounted for pivotal movement by virtue of pins located on the movable jaw and recesses in the fixed jaw. While this connector functions adequately, its capacity to remain assembled could be improved.

That connector is assembled by 1) placing the spring between proximal end portions of the fixed and movable jaws, and 2) then sliding the movable jaw generally along the longitudinal axis of the fixed jaw until the pins of the movable jaw are seated in the recesses of the fixed jaw. The portions of the recesses in the fixed jaw that are adapted to receive the pins are larger than the pins in the movable jaw. Because of the shape and size of the recesses of the fixed jaw, it was possible to move the movable jaw downward relative to the fixed jaw when the jaws were assembled (e.g. such as when a user intended to open the jaws). Although it generally does not pose a problem, such downward movement of the movable jaw relative to the fixed jaw could lead to inadvertent disassembly of the assembled jaws, clearly an undesirable result.

BRIEF DESCRIPTION OF THE INVENTION

The present invention provides a connector for a biomedical electrode having a generally flat, electrically conductive contacting tab. The connector comprises fixed and movable jaws having tab engagement surfaces for engaging the contacting tab of the biomedical electrode.

A means is provided for assembling the fixed and movable jaws in an assembled condition, and for mounting the jaws for relative pivotal movement between tab accept and closed positions. In the tab accept position, the movable jaw is spaced from the fixed jaw so that the tab of the biomedical electrode may be received between the jaws. In the closed position, the fixed and movable jaws are spaced more closely than in the tab accept position. That means preferably comprises the movable jaw having at least one pin (preferably two) and the fixed jaw having recesses for receiving the pins.

The connector according to the present invention preferably has a pair of securing ribs on the movable jaw that retain the jaws in the assembled condition. The recesses preferably comprise surfaces defining entry and locking portions. In a preferred embodiment, the locking portions of the recesses are oriented at approximately a 90° angle to the entry portions.

Preferably, the connector comprises a ramp within each of the recesses which separates the entry and locking portions and which terminates in a locking shoulder. The ramps become more shallow within their respective recesses proceeding from their distal ends to their proximal ends.

The entry portion has surfaces defining a pivot recess for receiving the pins of the movable jaw to afford the relative pivotal movement. The pivot recess has seating surfaces that resist downward movement of the pins when the pins are received in the pivot recess.

The connector is assembled by inserting the securing ribs and pins into the entry portion of their respective entry recesses, then pushing the securing ribs through a press-fit with the ramps, leaving the securing ribs trapped within the locking portions by the locking shoulders. To facilitate this mode of assembly, each of the securing ribs preferably have a chamfered lead-in surface adapted to facilitate the pushing of the securing ribs through the press-fit. In the assembled condition, the locking shoulders of the recesses are adapted to abut the securing ribs to resist disassembly of the movable and fixed jaws.

In a preferred embodiment, the locking shoulder is a substantially arcuate surface to afford the pivotal movement between the jaws. The locking portions are bounded by the locking shoulders, and the securing ribs are free to move within the locking portions so that the pins are held closely adjacent the pivot recess throughout a range of pivotal motion of the movable jaw with respect to the fixed jaw around the axis of the pins.

Preferably the fixed jaw comprises smooth, continuous tab engagement and lead-in surfaces, and the movable jaw comprises a tooth portion having a tab engagement surface, and a smooth lead-in surface. The tooth portion preferably comprises two teeth having a groove therebetween.

The present invention provides a connector which: 1) provides an actuation force less than about nine (9) pounds so that a broad range of user's may open the jaws of the connector while maintaining a desirable tab retention force, 2) preferably provides smooth tab engagement surfaces on one jaw which restrict damage to the tab of the electrode and which facilitate insertion of the tab between the jaws of the connector, 3) preferably provides a jaw with a continuous tab engagement surface to restrict excessive deflection of the tab of the electrode when it is clamped between the jaws of the connector to thereby restrict damage to the tab of the electrode, 4) may be constructed from X-Ray translucent materials, 5) is particularly suitable for use with a tab-style electrode comprising a tab with a stiff-flexible layer and a flexible-deformable second layer, 6) restricts the likelihood that the connector and its leadwire may become entangled with another connector/leadwire assembly or itself, 7) presents a low-profile which results in numerous advantages including comfort for the patient, 8) includes grasping or "manual activation" surfaces which conform to the shape of a user's digits, 9) is free of sharp surfaces that might cause discomfort for a patient should the patient be bumped in the vicinity of the connector or should the patient lie on the connector, and 10) provides for a connector that is readily assembled, but where the fixed and the movable jaws are pivotally attached to each other securely.

BRIEF DESCRIPTION OF THE DRAWING

The present invention will be further described with reference to the accompanying drawing wherein like reference numerals refer to like parts in the several views, and wherein:

FIG. 2 is a top view of a first embodiment of connector according to the present invention illustrating a portion of a leadwire;

FIG. 3 is a reduced sectional view of the connector of FIG. 2 taken approximately along lines 3—3 of FIG. 2, but which illustrates an unsectioned spring, and which illustrates fixed and movable jaws in a closed position;

FIG. 4 is a reduced sectional view similar to FIG. 3 except that FIG. 4 illustrates an electrically conductive tab of a biomedical electrode clamped between the fixed and movable jaws;

DETAILED DESCRIPTION

Figure 1:
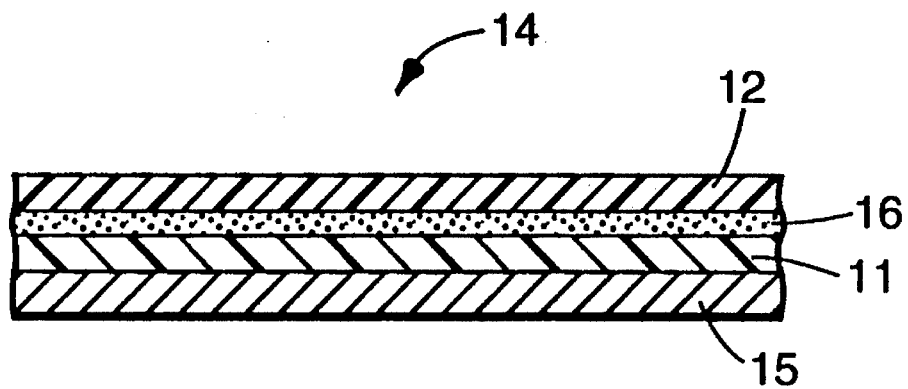
FIG. 1 is an exaggerated schematic view of portions of the electrically conductive tab of one example of biomedical electrode for use with the connector of the present invention.
Figure 7:
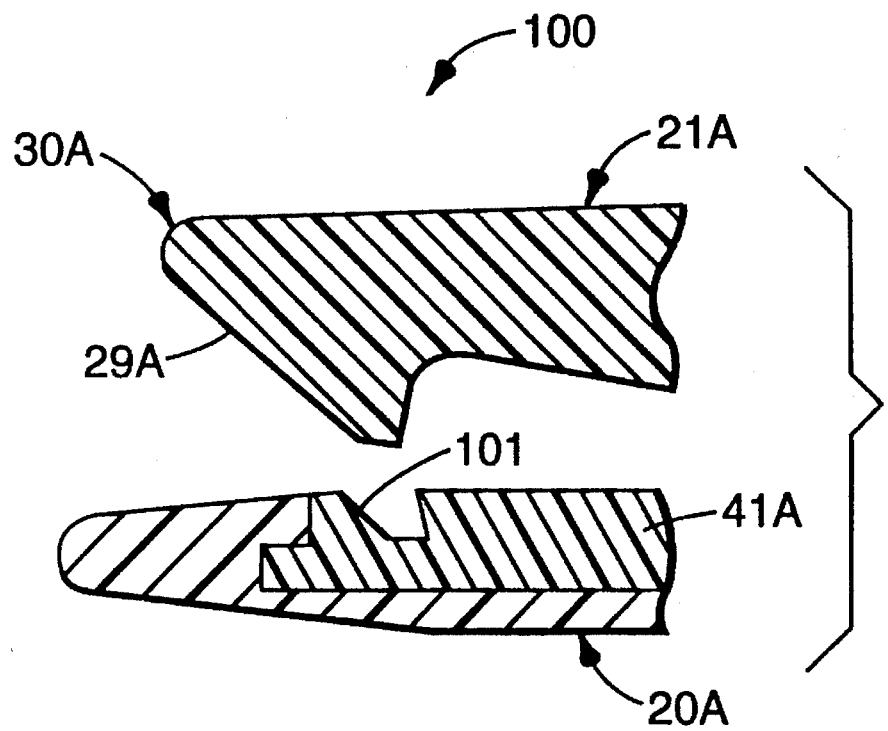
FIG. 7 is a partial cross section view of a distal end of fixed and movable jaws of a second embodiment of connector according to the present invention.
Figure 5:
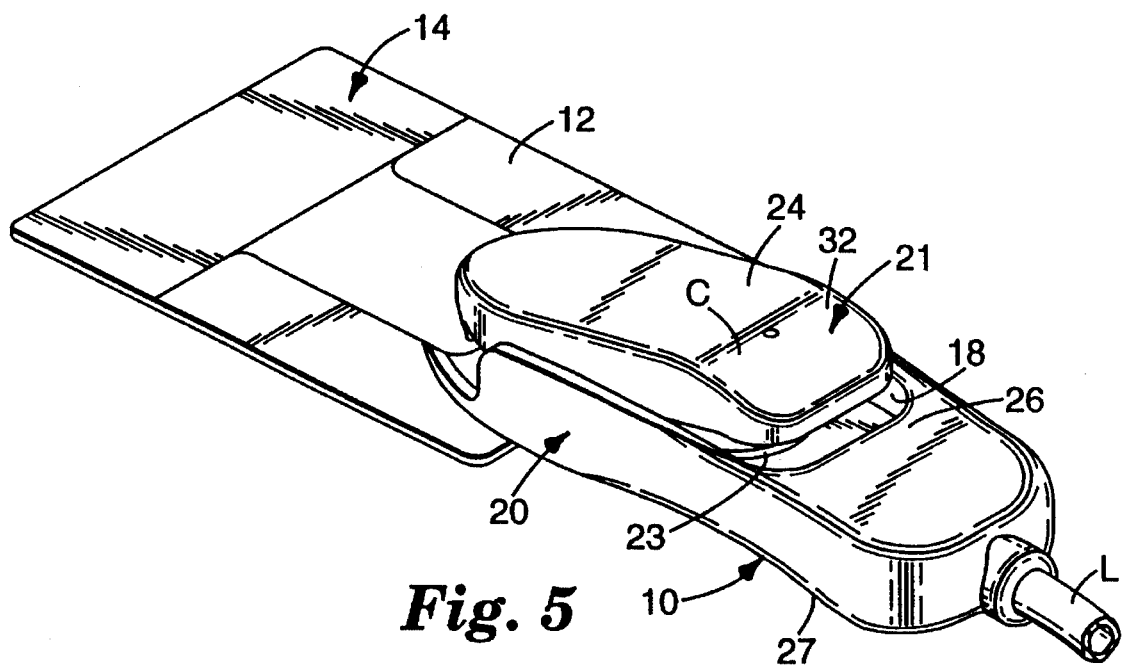
FIG. 5 is a perspective view of the connector of FIG. 2 illustrating an electrically conductive tab of a biomedical electrode clamped between the fixed and movable jaws.

FIGS. 2 through 6 of the drawing show a first embodiment of connector according to the present invention generally designated by the reference character 10. The connector 10 is adapted for use with a biomedical electrode having an electrically conductive contacting tab.

Examples of suitable biomedical electrodes are found in U.S. Pat. Nos. 4,543,958 to Cartmel, 4,798,208 to Faasse, Jr., 5,012,810 to Strand et al., 5,078,138 to Strand et al., 5,078,139 to Strand et al., 5,133,355 to Strand et al.; 5,133,356 to Bryan et al., and 5,215,087 to Anderson, the entire contents of which are herein expressly incorporated by reference. The connector 10 may be used with biomedical electrodes having widely varying thicknesses of electrically conductive tabs.

The connector 10 is particularly suitable for use with a biomedical electrode 14 having a firm, but flexible layer and a deformable layer. In particular, the biomedical electrode may comprise the electrode described in U.S. Pat. No. 5,133,356 to Bryan et al. the entire contents of which are herein expressly incorporated by reference.

FIG. 1 is a schematic illustration of a portion of the electrically conductive contacting tab of a biomedical electrode 14 having a firm, but flexible layer 11 and a deformable layer 12. The material used to construct the firm, flexible layer 11 preferably is constructed from a material that resists substantial permanent plastic deformation under forces exerted by the jaws of a connector, and is compatible with known processes for vapor coating silver. Such processes are used to coat a silver/silver chloride conductive coating 15 onto the layer 11.

Suitable materials for the layer 11 include, but are not limited to Scotchpar brand 3 mil PET film, commercially available from the Minnesota Mining and Manufacturing Co. (3M) of St. Paul, Minn., a polyester film commercially available as "Melinex" 505-300, 329 or 339 film from ICI Americas of Hopewell, Va. (coated with a silver/silver chloride ink commercially available as "R-300" ink from Ercon, Inc. of Waltham, Mass.), or a web of polyester/cellulose fibers commercially available as "Manniweb" web from Lydall, Inc. of Troy, N.Y. (having a carbon ink commercially available as "SS24636" ink from Acheson Colloids Company of Port Huron, Mich.).

Preferably, the material used to construct layer 11 is a 3 mil (0.075 mm) thick strip of polyethylene terephthalate film. The properties of the film included a tensile strength of about 28,000 psi in a machine direction, approximately 35,000 psi in the transverse direction, both as measured according to ASTM D882A. The coefficient of dynamic friction of this film is about 0.5 as measured by ASTM D1894. The commercial source of this film is ICI Films of Wilmington, Del., branded as "Melinex" 505.

The deformable layer 12 should be substantially softer than the layer 11 so that the layer 12 deforms in response to being clamped by the jaws of the connector 10. The deformable layer 12 enhances mechanical contact between the connector 10 and the electrode 14.

The layer 12 is adhered to the layer 11 by a layer of adhesive 16 such as a conventional acrylate adhesive. The adhesive may comprise a layer of 95.5%/4.5% isooctyl acrylate/acrylic acid copolymer adhesive, coated to a weight of 920 mg/200 cm² of backing area. However, any suitable adhesive may be utilized so long as the adhesive resists shear between the layers 11 and 12 and is compatible with the materials used to construct the layers 11 and 12.

Suitable materials for the layer 12 include, but are not limited to, a low density polyethylene such as NA 964-226, commercially available from Quantum Chemical of Rolling Meadows, Ill. This material may be extruded into a film with a thickness between about 0.002 to about 0.007 inches (0.005 to 0.013 cm), and preferably has a hardness of about 48 on the Shore D scale when measured according to ASTM Standard D2240, and in selecting alternative materials, those having a hardness between about 45 to 55 Shore D are believed to be particularly suitable. The commercial source of the layer 12 and adhesive 16 tape is Minnesota Mining and Manufacturing (3M) Company, of St. Paul, Minn., branded as "Blenderm" tape.

Referring now to FIGS. 2 through 6 of the drawings, there is shown the connector 10. The connector 10 comprises fixed 20 and movable 21 jaws, and a pivotal mounting means for mounting the movable jaw 21 for pivotal movement relative to the fixed jaw 20 between a tab accept position with the fixed jaw 20 spaced from the movable jaw 21 so that the tab of the biomedical electrode (e.g. 14) may be received between the jaws 20 and 21, and a closed position (FIG. 3) with fixed 20 and movable 21 jaws spaced more closely than in the tab accept position.

The movable jaw 21 comprises proximal and distal ends, a top surface 24 and a bottom surface 25. The fixed jaw 20 comprises a bottom surface 27, proximal and distal end portions terminating in proximal and distal ends with the proximal end portion having a top surface 26. At the proximal end of the fixed jaw 20, the connector is adapted to be connected to a leadwire L having an outside diameter.

The connector 10 is elongate and has a longitudinal axis along its length (preferably about 1.5 inches). The connector 10 has an overall height (preferably about 0.38 inches, but should be less than about 1.5 inches and more preferably less than about 0.5 inches) presenting a low profile connector and an overall width (preferably about 0.54 inches). The overall width is preferably at least 1.1 times greater than the overall height of the connector. Providing a connector with an overall width that is greater than its height is believed to provide a connector with resists rolling about its longitudinal axis.

The connector 10 may optionally include various features which conform the connector's operative surfaces to the general shape of a user's hand. For example, the bottom surface 27 of the fixed jaw 20 comprises an arcuate portion for conforming to the shape of a user's digits. For example the arcuate portion may be arcuate about an axis that is perpendicular to the longitudinal axis of the connector 10 and may have a radius of curvature of about 1.00 inches. The vertical distance from the top of surface 27 in FIG. 3 to its bottom is preferably about 0.06 inches.

The manually engagable actuation surface 32 may optionally include a locating means for assisting users in placing their digits in the desired position on the movable jaw 21. The locating means may comprise a rib, detent, depression, groove or slot in the desired position on the top surface 24 of the movable jaw 21.

The pivotal mounting means comprises a recess portion 18 recessed from the top surface 26 of the fixed jaw 20, and a pin 19 situated between the proximal and distal ends of the movable jaw 21 so that the movable jaw 21 can pivot about the axis of the pin 19. Preferably, the pin 19 may be integrally molded with the movable jaw 21 so that the pin and movable jaw form one, monolithic piece. Alternatively, the pin may comprise a metal pin adapted to be received in a slot in the movable jaw and fixed jaw.

The pin 19 is adapted to be received in a pivot groove in the fixed jaw 20 so that the movable jaw 21 can pivot about the axis of the pin 19 when a user manually presses on actuation surface 32. As best seen in FIG. 4, the pin 19 is situated to allow the tab of the electrode to be situated directly between the pin 19 and the fixed jaw 20. When it is said that the tab of the electrode is situated "directly between" the pin 19 and the fixed jaw 20, it is meant that, in FIG. 4, if a line is drawn vertically through the pin 19 and jaw 20, it would intersect a portion of the electrode's tab. This feature of the present invention affords the use of the connector 10 for a variety of sizes of tabs and also affords full insertion of the tab into the connector.

In the closed position (FIG. 3), the distance D between the top surface 26 of the fixed jaw 20 and the bottom surface 25 of the movable jaw 21 at the proximal end of the movable jaw 21 is less than the outside diameter of the leadwire L. For example, the distance D may be approximately 0.06 inches. This feature of the present invention restricts the chances that a leadwire L will become caught between the movable and fixed jaws of a connector, thereby restricting the chances that the connector 10 will become entangled with a leadwire L.

Another feature of the present invention that restricts the chances that the connector 10 will become entangled with a leadwire L is that the movable jaw 21 comprises a cam surface C generally adjacent its proximal end (See FIGS. 3 and 4). As shown in FIG. 3, the cam surface C is situated at an acute angle (alpha) relative to the top surface 26 of the fixed jaw 20. Thus, it is believed that when a leadwire L comes into contact with the cam surface C, the cam surface C will tend to move the leadwire L away from the recess portion 18 and away from becoming caught between the movable jaw 21 and fixed jaw 20.

The connector 10 also includes a biasing means such as a coil spring 23 for biasing the movable jaw 21 toward the closed position. While the biasing means is shown as a coil spring, it should be noted that the biasing means may comprise any suitable biasing means such as, but not limited to a leaf spring, a leaf spring integrally molded into the fixed jaw, an elastomeric structure (e.g. an egg shaped elastomer between the fixed and movable jaws), or a torsion spring so long as the movable jaw is biased toward the closed position. The coil spring may be constructed from any suitable material such as a plastic or metal. Optionally, the coil spring may be constructed from a substantially X-ray translucent material such as, Hytrel 5556 or Hytrel 7246 polyester elastomers generally available from DuPont of Delaware.

As shown in FIGS. 3 and 4, preferably the fixed jaw 20 has a smooth, continuous tab engagement surface 28; and the movable jaw 29 has a tooth portion 30 with a tab engagement surface 31, and a manually engagable actuation surface 32. However, it should be noted that the position of the tooth portion and the smooth, continuous tab engagement surface may be reversed, that is, the movable jaw may have a smooth, continuous tab engagement surface and the fixed jaw may have the tooth portion.

Both the movable jaw 21 and the fixed jaw 20 have a smooth lead-in surface 29. Preferably, the lead-in surfaces 29 are continuous, generally planar surfaces and form an angle therebetween of about 40 degrees.

As used herein, when it is said that a surface is "smooth" surface (e.g. the tab engagement or lead-in surfaces), it is meant that the particularly referenced surface is free of any rough surfaces such as teeth, cylindrically shaped terminal portions, abutment surfaces, labyrinth-like or tortuous paths, or otherwise rough surface that may substantially deform, bend or deflect an electrode contacting tab during insertion of the tab into the jaws of the connector. A "smooth" tab engagement surface or lead-in surface is preferably a generally planar surface, but may comprise a slightly arcuate surface so long as the surface does not present a structure that is likely to bend, deform or otherwise deflect the electrode tab upon its insertion between the jaws of the connector.

As used herein, when it is said that a surface is a "continuous" surface (e.g. a tab engagement surface), it is meant that the particularly referenced tab engagement surface is free of any discontinuities such as a hole, depression, groove, slot, slit or other discontinuous surfaces which tend to substantially deflect the conductive tab of the electrode when it is clamped between the jaws of the connector. Such deflection may mar, puncture or otherwise damage the conductive surface of the electrically conductive contacting tab of the biomedical electrode that may potentially result in a loss of continuity or may otherwise adversely affect the electrical properties of the biomedical electrode. The discontinuity may also substantially deform, bend or deflect an electrode contacting tab during insertion of the tab into the jaws of the connector with the attendant disadvantages described above.

The fixed and movable jaws 20 and 21 comprise distal end portions having generally arcuate surfaces terminating in distal ends. The arcuate surfaces present blunt surfaces to a patient which reduces the chances that the connector will cause discomfort for the patient. The distal end of the movable jaw 21 is spaced proximally from the distal end of the fixed jaw 20.

In addition to the smooth lead-in surfaces 29, the connector 10 also includes several features which further assist a user in placing the tab of the electrode between the fixed and movable jaws 20 and 21. For example, at each position along the longitudinal axis of the connector 10, the fixed jaw 20 is wider than the movable jaw 21. When the connector 10 is viewed from a top plane (as the connector is in FIG. 2), the distal end portion of the fixed jaw 20 encompasses the distal end portion of the movable jaw 21. In this view, a user can determine when a tab is placed between the movable and fixed jaws 20 and 21 as, when a tab is placed between the movable and fixed jaws, a portion of the fixed jaw 20 will no longer be seen as the tab will block a user's view. In this manner, the connector 10 facilitates insertion of the tab between the jaws. Optionally, the movable jaw 21 may have a hole 103 (seen in FIG. 2) in its distal end portion for viewing the relative position of the tab of the electrode and the jaws of the connector.

Figure 6:
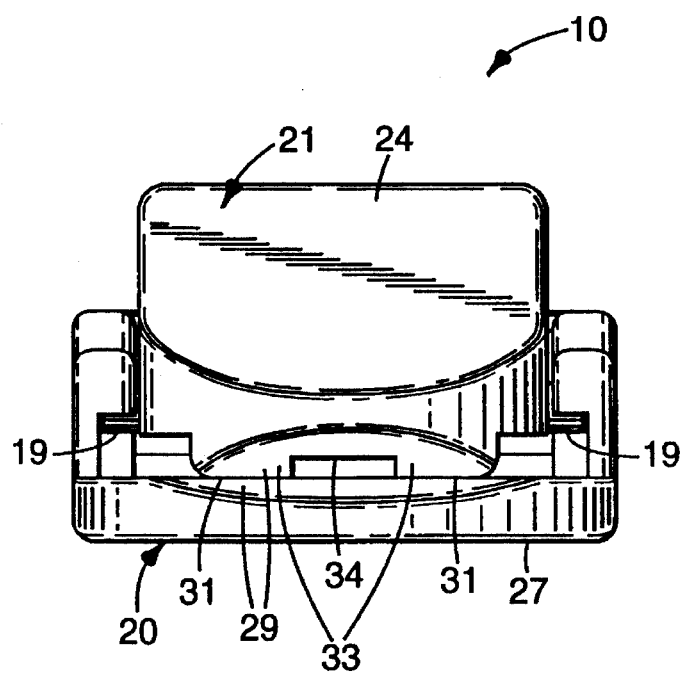
FIG. 6 is an enlarged front end view of the connector of FIG. 2 illustrating fixed and movable jaws in a closed position.

The tooth portion 30 preferably comprises a pair of teeth 33 as best seen in FIG. 6. The teeth 33 have a groove 34 therebetween, and each of the teeth 33 have a tab engagement surface 31. The groove 34 is believed to be particularly desirable when the connector 10 is used with a tab having a deformable layer 12 (e.g. a tab similar to the tab shown in FIG. 1). It is believed that some of the material 12 may enter the groove 34 and enhance the holding properties of the connector 10.

Each of the teeth 33 have a rear ridge surface 39. The rear ridge surfaces 39 are preferably situated generally perpendicular relative to a horizontal line with reference to FIG. 3. A perpendicular rear ridge surface tends to beneficially grasp the electrode tab, particularly when the electrode tab has a deformable layer such as the layer 12 shown in FIG. 1. At most, the ridge surfaces 39 should be inclined at an angle of between more than about 60 degrees and less than about 120 degrees relative to a horizontal line with reference to FIG. 3. If the angle is less than 60 degrees, the ridge surface 39 tends to act as a camming surface to open the jaws when an electrode 14 with a flexible layer (e.g. 12) is pulled longitudinally from the jaws of the connector, clearly an undesirable result. If the angle is more than 120 degrees, than the movable jaw 21 becomes difficult to construct as the shape becomes complicated.

Preferably, the connector 10 has electrically conductive plates or plastic inserts 41 and 42 which place the distal end portion of the fixed jaw 20 in electrical contact with the leadwire L. For example, the conductive plates 41 and 42 may be injection molded of a conductive material such as, a 40 percent (%) carbon fiber reinforced Acrylonitrile-Butadiene-Styrene material, sold under the name RTP 687 generally available from RTP Co. of Winona Minnesota (which is also a substantially X-ray translucent material). Although they are shown as two separate plates, the conductive plates 41 and 42 preferably comprise a single, monolithic conductive plate constructed from the same material. Preferably, the distal end of the fixed jaw 20 has a lip portion which helps retain the plates 41 and 42 in the fixed jaw 20. Gripping tabs 45 may be molded into fixed jaw 20 for the purpose of gripping the leadwire L.

Also preferably, the movable jaw 21 and portions of the fixed jaw 20 are constructed from a material which need not be an electrically conductive material (as long as the fixed jaw also includes conductive plastic inserts). Suitable materials includes plastics, metals and polymers. Preferably, the movable jaw 21 and portions of the fixed jaw 20 are constructed from Delrin material generally available from DuPont (which is substantially X-ray translucent). However, it should be pointed out that, optionally, the movable jaw may be constructed from an electrically conductive material such as the material used to construct conductive plastic inserts 41 and 42. Also optionally, the spring 23 may be constructed from an electrically conductive material.

Figure 8:
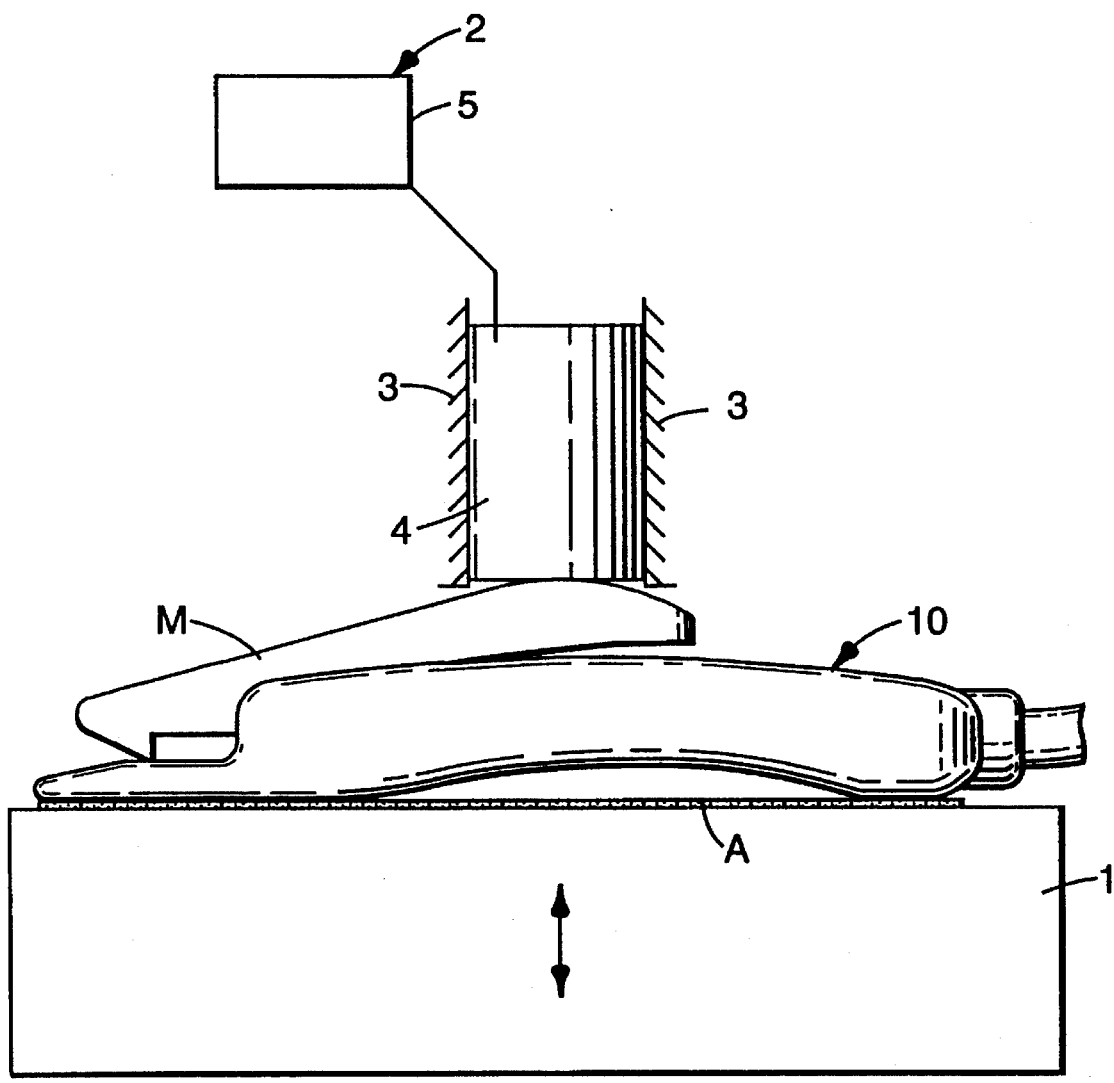
FIG. 8 is a schematic illustration of the test equipment used to conduct tab release and actuation force tests according to the present invention.

Referring now to FIG. 8 of the drawings, there is shown a second embodiment of connector according to the present invention generally designated by reference character 100. The connector 100 includes many features that are generally identical to the connector 10 and which have been given the same reference character to which the suffix "A" has been added.

Unlike the connector 10, in the connector 100, the fixed jaw 20A, and more particularly the conductive plate 41A has a recess 101 adapted to receive the ridge of the tooth portion. Generally speaking, the connector 100 is believed to exhibit a higher tab release force than the connector 10. However, it is believed to be more difficult to insert a tab of an electrode between the jaws 20A and 21A of the connector 100 as the tab can be caught in the recess 101 and bent.

TEST RESULTS

A connector of the type described with reference to FIGS. 2 through 6 was made as follows. The axis of the spring 23 was situated approximately 0.31 inches from the axis of the pin 19. The distance between the axis of the pin 19 and teeth 33 was approximately 0.22 inches. The total surface area of the tab engagement surfaces of the teeth was approximately 0.016 square inches. The above described connector is hereafter referred to as Connector A.

Connector B comprises an alligator type clip number M306L10 generally available from the Minnesota Mining and Manufacturing Co. (3M) of St. Paul, Minn. (or alternatively Hershman, of Germany). Connector C comprises an Alligator clip number J5 generally available from the Minnesota Mining and Manufacturing Co. (3M) of St. Paul, Minn. (or alternatively Hershman, of Germany). Connector D comprises an alligator type clip number S106L10 generally available from the Minnesota Mining and Manufacturing Co. (3M) of St. Paul, Minn. or model No. 6A2A1A21 generally available from Tronomed, Inc. of Laguna Hills, Calif. Connector E comprises a clip similar to the clip shown in U.S. Pat. No. 4,797,125 believed to have been generally available from Tronomed, Inc. of Laguna Hills, Calif. Connector F comprises a DURALINC™ clip number 2B2A1A21 generally available from Tronomed, Inc. of Laguna Hills, Calif. Connector G comprises an Astro-Trace™ clip believed generally available from LeBlanc.

ACTUATION FORCE MEASUREMENTS

FIG. 8 is a schematic illustration of test equipment used to record actuation force measurements for the various connectors. The test equipment included a base 1, a digital force gauge 2 with jig 3, probe 4 and readout 5.

A connector to be measured was placed on the base 1 with a double sided adhesive tape A (optionally a clamp may be used) so that the movable jaw M of the connector was accessible. The movable jaw of the connector was then depressed using a digital force gauge 2, held in jig 3 allowing precision movement. In particular, the Model DFI-50 digital force gauge, commercially available from Chatilion, was used. The probe 4 of the force gauge was manually situated so that it was centered against the uppermost point of the normal finger position for opening the connector in the manner shown schematically in FIG. 8, and additional force was applied in a direction generally normal to the base 1. The force required to open the connector to its widest normal position was noted on readout 5.

The widest normal position is defined herein as the position wherein (1) the distal ends of the fixed and movable jaws are at their maximum separation due to interference of the spring itself, or (2) the distal ends of the fixed and movable jaws are at their maximum separation due to physical interference between portions of the fixed and movable jaws, or (3) the distal ends of the fixed and movable jaws are at their maximum separation due to other factors.

It is believed that ideally, the actuation force of the present invention should be at most about 9 pounds to facilitate easy opening of the jaws of the connector to its widest normal position. If the actuation force is above about 9 pounds, some users may have difficulty in using the connector, particularly those users who suffer from an ailment such as arthritis which adversely affect's their ability to squeeze an object. Table 1 illustrates a the results of actuation force tests run on the various connectors described above.

TAB RELEASE FORCE TEST

A test strip was created by providing a 3 mil (0.075 mm) thick strip of polyethylene terephthalate film 0.375 inches (0.94 cm) wide in the machine direction of the film by 2 inches (5 cm) long in the transverse direction of the film. The properties of the film included a tensile strength of 28,000 psi in the machine direction, 35,000 psi in the transverse direction, both as measured according to ASTM D882A.

The coefficient of dynamic friction of this film was 0.5 as measured by ASTM D1894. The commercial source of this film was ICI Films of Wilmington, Del., branded as Melinex 505.

To this strip was laminated an adhesive tape composed of a backing of low density polyethylene film having a hardness of 48 on the Shore D scale according to ASTM 2240. The adhesive was a layer of 95.5%/4.5% isooctyl acrylate/ acrylic acid copolymer adhesive, coated to a weight of 920 mg/200 cm$^2$ of backing area. The total thickness of the finished tape was 0.005 inches (0.12 mm). The commercial source of this tape was the 3M Company, of St. Paul, Minn., branded as Blenderm tape. The total thickness of the finished test strip was 0.008 inches.

A connector to be tested was used to grasp the test strip along the width axis, and was then clamped in the fixed jaw of an Instron force testing machine. The other end of the test strip was them clamped in the moving jaw of the machine, and the speed of the moving jaw was set to 30.1 cm/minute. The peak force measured before the strip was pulled free of the connector during tensile loading was measured.

It is believed that ideally, the tab release force of the present invention should be at least about 2 pounds. A tab release force of about 2 pounds is believed to be suitable for a wide variety of uses of the connector 10. If the tab release force is below about 2 pounds, then it is believed that the tab of the electrode may be easily dislodged from the connector, clearly a disadvantageous result. Table 1 illustrates the results of tab release force tests run on the various connectors described above.

TABLE 1

| Connector | Tab Release Force (Pull-off Force) (Pounds) | Actuation Force (Pounds) |
| --- | --- | --- |
| Clip A (Present Invention) | (3.9) | 3.3 |
| Clip B | (.5) | 3.0 |
| Clip C | (1.3) | 3.0 |
| Clip D | (.8) | 10.2 |
| Clip E | (1.0) | 12.5 |
| Clip F | (4.6) | 28.3 |
| Clip G | (1.0) | 11.6 |

ALTERNATE EMBODIMENT SUITABLE FOR RAPID ASSEMBLY

Figure 9:
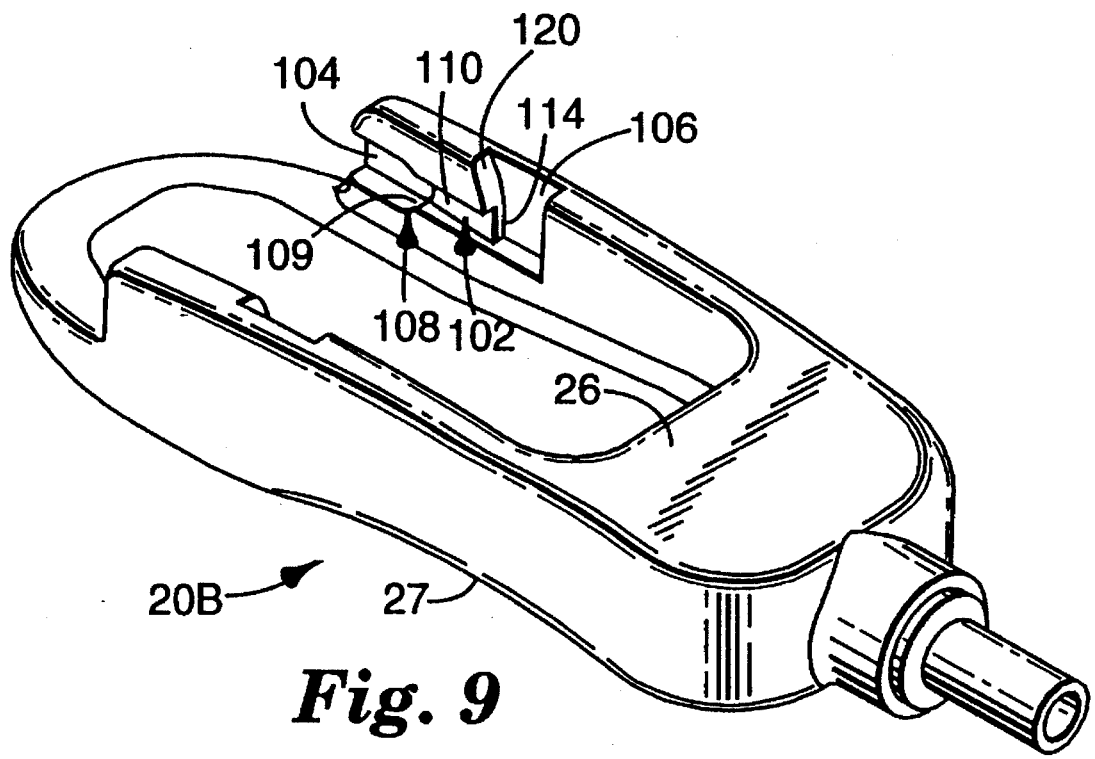
FIG. 9 is a perspective view of a fixed jaw suitable for use in an alternate embodiment of the present invention.
Figure 10:
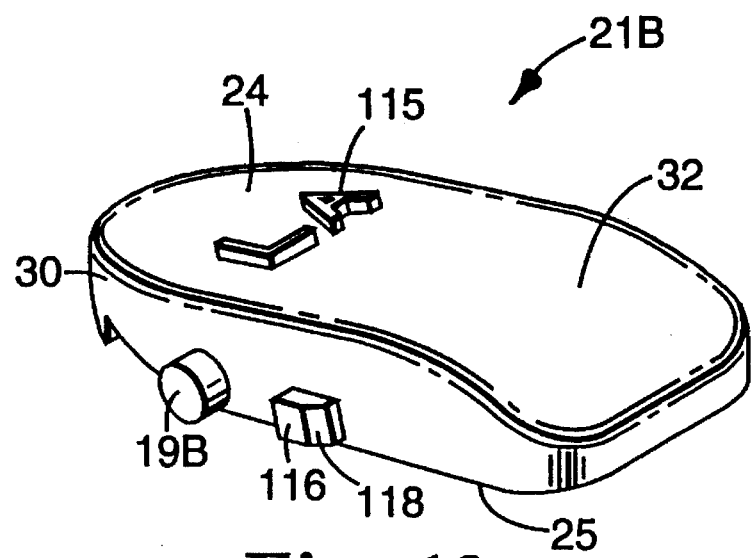
FIG. 10 is a perspective view of a movable jaw suitable for use in conjunction with the fixed jaw of FIG. 9.

Referring now to FIG. 9, a perspective view of a fixed jaw 20B suitable for use in an alternate, easily assembled, embodiment of a connector according to the present invention is shown. In FIG. 10, a perspective view of a movable jaw 21B for use with the fixed jaw 20B is shown.

The connector is generally designated by reference character 10B in FIGS. 11–15. The connector 10B includes many features that are generally identical to the connector 10 and which have been given the same reference character to which the suffix "B" has been added.

The connector 10B comprises a fixed jaw 20B and a movable jaw 21B. Like the previously described embodiments, the fixed 20B and movable 21B jaws have tab engagement surfaces for engaging the contacting tab of the biomedical electrode. The fixed jaw 20B comprises a bottom surface 27, proximal and distal end portions terminating in proximal and distal ends with the proximal end portion having a top surface 26. At the proximal end of the fixed jaw 20B, the connector 10B is adapted to be connected to a leadwire having an outside diameter L.

Now referring to FIG. 10, a perspective view of the movable jaw 21B is shown. The movable jaw 21B comprises proximal and distal ends, a top surface 24 and a bottom surface 25. Optionally, indicia 115 may appear on top surface 24 to indicate the location of placement on the body on the electrode to which the connector 10B is attached.

Pins 19B and locking or securing ribs 116 (discussed in greater detail below in conjunction with an assembly means as defined herein) are provided. In preferred embodiments, the securing ribs 116 will have a chamfered lead-in surface 118. Preferably, the pins 19B and the securing ribs 116 may be integrally molded with the movable jaw 21B so that the pin and movable jaw form one, monolithic piece.

The connector 10B comprises an assembly means for assembling the fixed and movable jaws in an assembled condition, and for mounting the jaws for relative pivotal movement between tab accept and closed positions. Unlike the previously described embodiments, the connector 10B comprises at least one securing rib 116 (preferably two) on one of the fixed 20B or movable 21B jaws (preferably the movable jaw 21B) for retaining the jaws in the assembled condition.

In the tab accept position, the distal end of the movable jaw 21B is spaced from the distal end of the fixed jaw 20B so that the tab of the biomedical electrode may be received between the jaws 20B and 21B. In the closed position, the distal ends of the fixed 20B and movable 21B jaws are spaced more closely than in the tab accept position.

The above described assembly means comprises one of the jaws (preferably the movable jaw 21B) having a pin (preferably a pair of pins 19B) and the other of the jaws (preferably the fixed jaw 20B) having a recess (preferably a pair of recesses 102) for receiving the pin 19B.

In the illustrated embodiment of FIGS. 9–15, the fixed jaw 20B has a pair of recesses 102 therein. The recesses 102 are located on opposite sides of the fixed jaw 20B and face each other. Each of these recesses 102 has an entry portion 104, and a locking portion 106. The locking portion 106 is conveniently oriented at approximately 90° to the entry portion 104. In the assembled condition, the surfaces defining the locking portions 106 of the recesses 102 are adapted to abut the securing ribs 116 to resist disassembly of the movable 21B and fixed 20B jaws.

Figure 15:
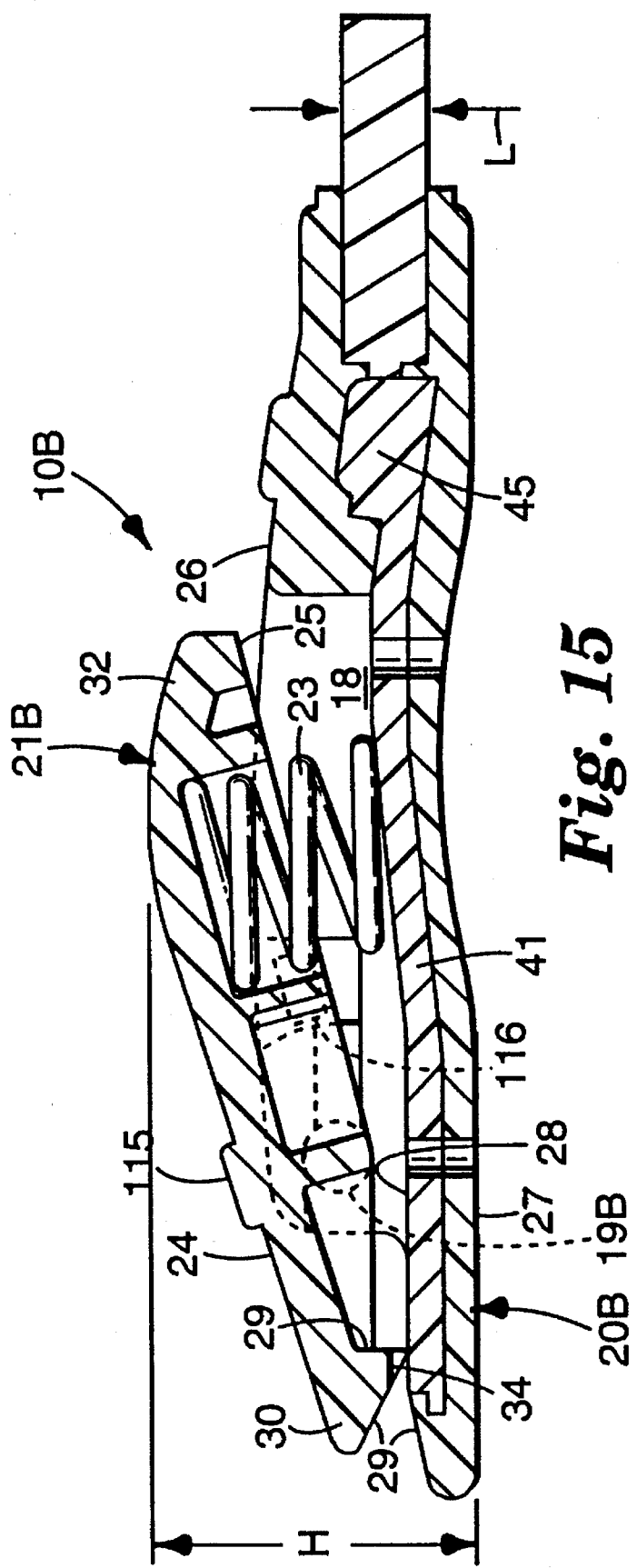
FIG. 15 is a cross-section view of an entire connector prepared from the jaws of FIGS. 9 and 10.

Referring now to FIG. 15, a cross-section view of a connector 10B in an assembled condition is depicted. Consistent with the previously identified embodiments, the connector 10B has a biasing means such as a coil spring 23 for biasing the jaws toward the closed position. The alternates discussed above with respect to the various suitable biasing means apply to this embodiment as well.

FIG. 15 illustrates that the height of the connector defines a connector height axis H when the jaws 20B and 21B are in the assembled condition. The particular sizes and relationships between the connector's height, width and length discussed above with respect to the various other embodiments apply to this embodiment as well.

The entry portions 104 have surfaces defining pivot recesses 108 for closely receiving the pins 19B of the movable jaw 21B to afford the relative pivotal movement between the jaws. The pivot recesses 108 have seating surfaces 109 that resist movement of the pins 19B in the downward direction (see FIG. 15) of the connector height axis H when the pins 19B are received in the pivot recess 108. This represents an advantage over the previously described embodiments as the seating surfaces 109 resist movement of the pins 19B along a downward direction parallel to the connector height axis H to further resist disassembly of the connector 10B. This feature is particularly advantageous as, in some circumstances, when users press on the proximal top surface 32 of the movable jaw 21B to open the connector 10B, they may generate a force that has the potential of disassembling the movable jaws.

Figure 12:
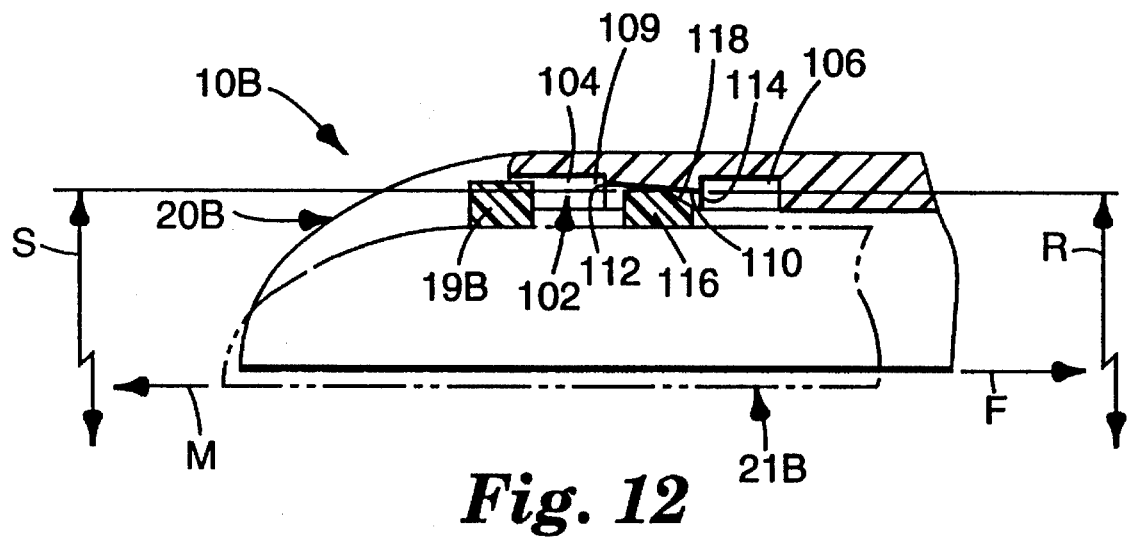
FIG. 12 is a cross-section top detail view of the intermediate stage in the assembly depicted in FIG. 11.

Referring now to FIG. 12, the fixed jaw 20B has a longitudinal axis F, and the movable jaw 21B also has a longitudinal axis M. The axes M and F are actually substantially parallel, but are shown in FIG. 12 as offset for purposes of illustration of these elements.

The ribs 116 define a rib width measured in a direction S (see FIG. 12) which is generally transverse to both the longitudinal axis M of said movable jaw and the connector height axis H. Referring to FIG. 12, the rib width is measured between the rib 116 shown in FIG. 12 and the opposite rib 116 (not shown in FIG. 12 but shown in FIG. 10) along the direction S.

The fixed jaw 20B has a pair of ramps 110 separating the entry 104 and locking 106 portions of the recesses 102. The ramps 110 have proximal 112 and distal 114 ends. Referring again to FIG. 12, the ramps 110 define a ramp width measured in a direction R which is generally transverse to both the longitudinal axis F of the fixed jaw 20B and the connector height H. The ramp width is measured between the ramp 110 shown in FIG. 12 and the opposite ramp.

Preferably the ramp width varies along at least a portion of the longitudinal axis F of the fixed jaw 20B and defines a minimum ramp width. The ramp width decreases proceeding from its distal 112 to its proximal 114 end. The minimum ramp width is found between the proximal ends 114 of the ramps 110.

In order for the assembly means to secure or "lock" the movable jaw 21B to the fixed jaw 20B, the rib width is made greater than the minimum ramp width. To assemble the connector 10B, the materials used to construct the ribs 116 and the ramps 110 should be flexible enough to afford passage of the ribs 116 from the distal side of the ramp 110 to its proximal side, yet resilient enough to avoid permanent deformation as the ribs 116 engage the proximal side of the ramp 110. Any of the materials noted above are believed to be suitable for use to construct the ramps 110 and ribs 116.

A preferred material includes Minlon which is a mineral filled Nylon 66, generally available from Dupont. Preferably the interference fit should be between about 0.017 inches and 0.037 inches, and more preferably the interference should be about 0.027 inches. However, the desired interference is affected by the material of the ramps 110 and pins 19B.

The ramps 110 have a locking shoulder 120 at their proximal ends 114. The locking shoulders 120 are preferably arcuate surfaces. The connector 10B is assembled by inserting the securing ribs 116 and pins 19B into the entry portions 104 of their respective recesses 102, then pushing the securing ribs 116 axially (M) through a press-fit with the ramps 110 so that the securing ribs 116 become positioned within the locking portion 106 of the recess 102 leaving the securing ribs 116 trapped within the locking portions 106 by the locking shoulders 120. During this step, the pins 19B become seated in the seating surfaces 109.

In the depicted embodiment, in order for this to happen, the ribs 116 must be pushed through a press fit with the proximal end or ramps 110. The chamfered lead-in surfaces 118 facilitate the pushing of the securing ribs 116 through the press-fit. Once the assembly movement is completed, the securing ribs 116 are captured within locking portions 106 because the ribs 116 are not chamfered for the reverse movement. The side of the ribs 116 opposite the lead in surfaces 118 are not chamfered so that the ribs 116 will abut the locking shoulder 120 to resist disassembly.

In the assembled condition, the pins 19B are settled into pivot sections 108, and held there by the interaction between the securing ribs 116 and the proximal end 114 of the ramp 110 (locking shoulder 120). As will be seen in FIG. 9, the proximal end 114 shades into locking shoulder 120 which helps define locking portion 106.

The locking portions 106 are bounded by the locking shoulders 120. The locking portion 120 is curved or arcuate to remain adjacent to the arc described by the ribs 116 as they move with movable jaw 21B in pivotal motion around the axis provided by pins 19B against pivot sections 108. The securing ribs 116 are free to move within the locking portions 106 so that the pins 19B are held closely adjacent the pivot recess 108 throughout a range of pivotal motion of the movable jaw 21B with respect to the fixed jaw 20B around the axis of the pins 19B.

Figure 11:
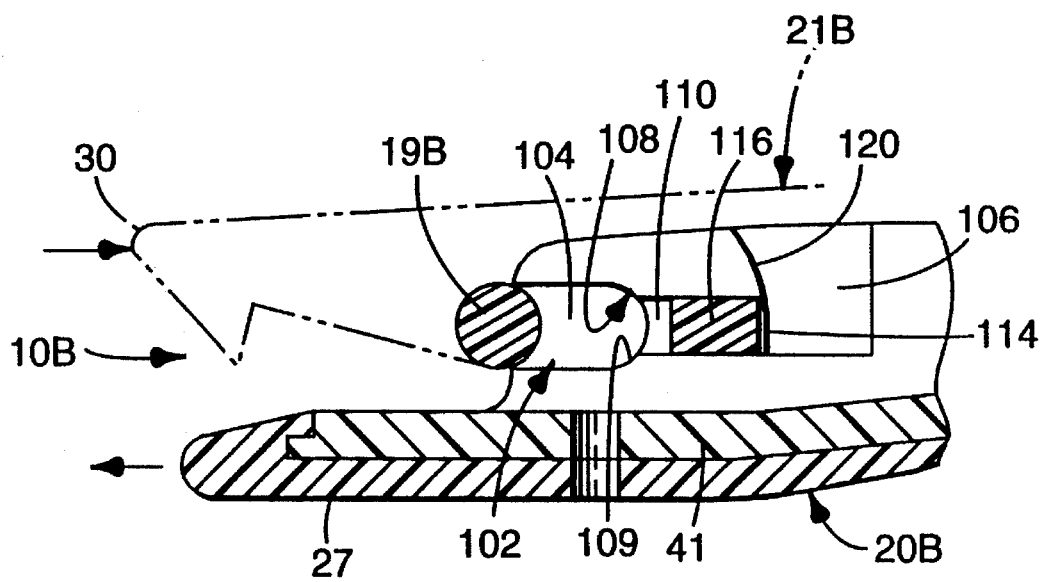
FIG. 11 is a cross-section side detail view of an intermediate stage in an assembly of the jaws of FIGS. 9 and 10.

Referring now to FIGS. 11 and 12, cross-section detail views of an intermediate stage in the assembly of the jaws of connector 10B are shown. For visual clarity, in these Figures, and in FIGS. 13 and 14, the outline of portions of the movable jaw 21B except for pin 19B and securing rib 116 is rendered in phantom. In FIG. 11, securing rib 116 has been inserted into entry portion 104, and is now press-fit against the proximal end of ramp 110. Trailing the securing rib 116 into the recess 102, the pin 19B is seen just at the entrance of the entry portion 104. In FIG. 12, the utility of chamfered end 118 in helping locking tab 116 begin its press-fit passage across ramp 110 starting a distal end 112 can be more readily appreciated.

Figure 13:
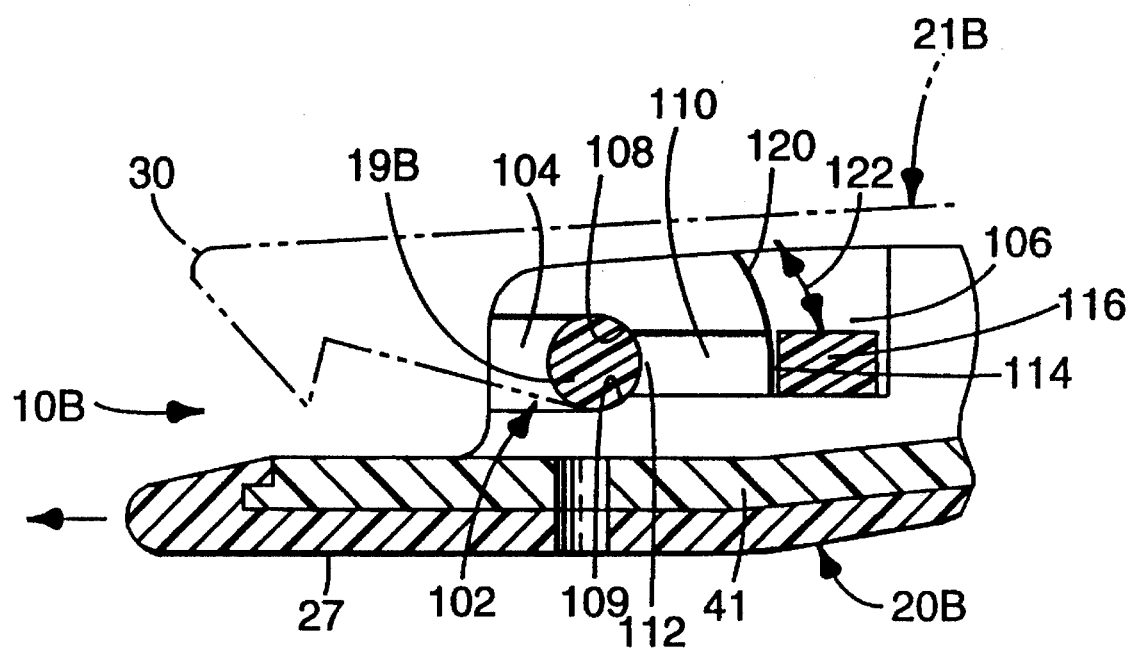
FIG. 13 is a cross-section side detail view when the assembly depicted in FIG. 11 is completed.
Figure 14:
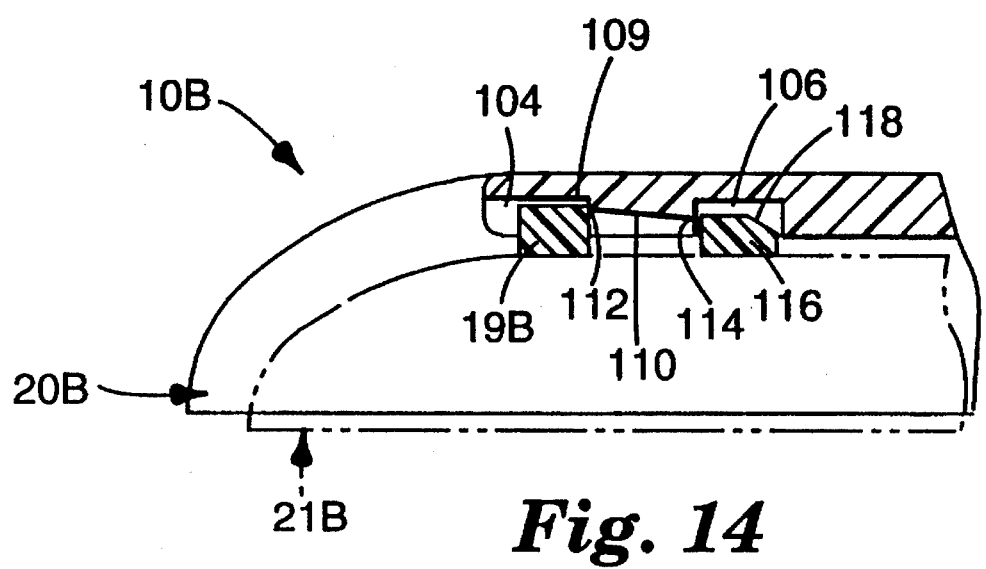
FIG. 14 is a cross-section top detail view of the completed assembly depicted in FIG. 13.

Referring now to FIGS. 13 and 14, cross-section detail views of the final stage after the assembly of the jaws of connector 10B depicted in FIGS. 11 and 12 has been completed are shown. In FIG. 13, it can more readily be appreciated how pin 19B is received or seated against pivot recess 108 to facilitate pivotal movement of movable jaw 21B relative to fixed jaw 20B. During such pivotal movement about the axis of pins 19B, securing rib 116 moves in the direction of arrow 122. Constrained by proximal end 114 and locking shoulder 120, the securing rib 116 has the necessary freedom to move while still holding movable jaw 21B in the assembled condition. In FIG. 14, it can be seen how securing rib 116 can no longer backtrack to the disassembled condition because of the interference between securing rib 116 and the highest edge of ramp 110 at proximal end 114 (the locking shoulder 120).

With the described alternate embodiment, the assembly is more readily accomplished, and the fixed and the movable jaws are secured to each other more robustly. This is accomplished without eschewing other desirable features available in other embodiments, for example the features which restrict the chances that the connector 10B will become entangled with a leadwire L, and the shapes of the distal ends of the jaws. Further, in this embodiment as well, the position of the tooth portion and the smooth, continuous tab engagement surface may be reversed, that is, the movable jaw may have a smooth, continuous tab engagement surface and the fixed jaw may have the tooth portion.

The following is an example of some measurements according to the present invention:

EXAMPLE 1

| FEATURE | SIZE (INCHES UNLESS STATED OTHERWISE) |
|---|---|
| Pin width between Pins 19B | 0.478 |
| Indiv. Max Pin 19B Diameter | 0.076 |
| Indiv. Pin 19B Protrusion | 0.091 |
| Minimum Ramp 110 Width | 0.435 |
| Connector Height H | 0.37 |
| Overall connector Width | 0.54 |
| Overall Length | 1.52 |
| Ramp 110 Width at Proximal End | 0.455 |
| Width between entry portions 104 | 0.42 |
| Max. Height of Entry Portion 104 | 0.08 |
| Spring Constant | 17 pounds/inch |
| Indiv. Max Rib 116 Diameter | 0.076 |
| Indiv. Rib 116 Protrusion | 0.038 |
| Rib 116 Width (between Ribs 116) | 0.463 |

The present invention has now been described with reference to several embodiments thereof. It will be apparent to those skilled in the art that many changes or additions can be made in the embodiments described without departing from the scope of the present invention. Thus, the scope of the present invention should not be limited to the structures described in this application, but only by structures described by the language of the claims and the equivalents of those structures.

What is claimed:

1. A connector for a biomedical electrode having an electrically conductive contacting tab, the connector comprising:
    fixed and movable jaws having tab engagement surfaces for engaging the contacting tab of the biomedical electrode, said fixed and movable jaws having proximal and distal ends,
    means for assembling the fixed and movable jaws in an assembled condition, and for mounting the jaws for relative pivotal movement between a) a tab accept position with the distal end of the movable jaw spaced from the distal end of the fixed jaw so that the tab of the biomedical electrode may be received between the jaws, and b) a closed position with distal ends of the fixed and movable jaws spaced more closely than in the tab accept position;
    said means comprising one of said jaws having at least one pin and the other of said jaws having at least one recess for receiving the at least one pin;
    biasing means for biasing the jaws toward the closed position;
    at least one securing rib on one of said fixed and movable jaws for retaining the jaws in the assembled condition, and
    said at least one securing rib being receivable in the at least one recess.

2. A connector for a biomedical electrode according to claim 1 wherein the at least one recess comprises a pair of recesses,
    the recesses comprise surfaces defining an entry portion and at least one locking portion, and
    wherein, in the assembled condition, the surface defining the at least one locking portion of the recesses is adapted to abut the securing rib to resist disassembly of the movable and fixed jaws.

3. A connector for a biomedical electrode according to claim 1 wherein the fixed and movable jaws have longitudinal axes, and said jaws defining a connector height axis in the assembled condition;
    said movable jaw has a pair of securing ribs, said ribs defining a rib width measured in a direction which is generally transverse to the longitudinal axis of said movable jaw and which is generally perpendicular to the connector height axis,
    said fixed jaw has a pair of recesses and said movable jaw has a pair of pins, the recesses comprising surfaces defining entry and locking portions.

4. A connector for a biomedical electrode according to claim 3 wherein:
    said fixed jaw has a pair of ramps separating said entry and locking portions of said recesses, said ramps having proximal and distal ends, the distance measured generally transverse to both the longitudinal axis and said connector height between said ramps defining a ramp width, said ramp width varying along at least a portion of the longitudinal axis of said fixed jaw and defining a minimum ramp width;
    wherein said rib width is greater than said minimum ramp width.

5. A connector for a biomedical electrode according to claim 3 wherein said recesses comprise entry portions having surfaces defining pivot recesses for receiving said pins of said movable jaw to afford said relative pivotal movement,
    said pivot recesses having seating surfaces that resist movement of said pins in the direction of the connector height when the pins are received in the pivot recesses.

6. A connector according to claim 1 wherein the fixed jaw is adapted to be connected to a leadwire, the fixed jaw having a pair of recesses for receiving the pins, said recesses comprising entry and locking portions; and further wherein the moveable jaw has two securing ribs thereon.

7. A connector according to claim 6 wherein the locking portions of the recesses are oriented at approximately a 90° angle to the entry portions.

8. A connector according to claim 7 wherein the connector further comprises a ramp within each of the recesses.

9. A connector according to claim 8 wherein the connector has proximal and distal ends, and wherein the ramps have a locking shoulder at their proximal ends.

10. A connector according to claim 9 wherein the connector is assembled by inserting the securing ribs and pins into the entry portion of their respective recesses, then pushing the securing ribs through a press-fit with the ramps, leaving the securing ribs trapped within the locking portions by the locking shoulders.

11. A connector according to claim 10 wherein the securing ribs have a chamfered lead-in surface adapted to facilitate the pushing of the securing ribs through the press-fit.

12. A connector according to claim 11 wherein the entry portions each have surfaces defining a pivot recess for receiving said pins of said movable jaw to afford said relative pivotal movement.

13. A connector according to claim 12 wherein the locking shoulder is a substantially arcuate surface to afford said pivotal movement, the locking portions are bounded by the locking shoulders, and further wherein the securing ribs are free to move within the locking portions so that the pins are held closely adjacent the pivot recess throughout a range of pivotal motion of the movable jaw with respect to the fixed jaw around the axis of the pins.

14. A connector according to claim 1 wherein said recesses and securing rib are constructed from materials which afford an interference fit.

15. A method of assembling a connector for a biomedical electrode having an electrically conductive contacting tab, the method comprising the steps of:

1) providing a connector having: a) fixed and movable jaws having tab engagement surfaces for engaging the contacting tab of the biomedical electrode, said fixed and movable jaws having proximal and distal ends, b) one of said jaws having a pair of pins and the other of said jaws having a pair of recesses for receiving the pins, the recesses comprising entry and locking portions separated by a locking shoulder and a ramp; and c) a pair of securing ribs on one of said fixed and movable jaws for retaining the jaws in the assembled condition;

2) inserting the securing ribs and pins into the entry portion of their respective recesses, then pushing the securing ribs through a press-fit with the ramps, leaving the securing ribs trapped within the locking portions by the locking shoulders.

16. A method according to claim 15 wherein the step including the step of: affording free movement of the securing ribs within the locking portions so that the pins are held closely adjacent the pivot recess throughout a range of pivotal motion of the movable jaw with respect to the fixed jaw around an axis of the pins.

17. A method according to claim 15 wherein the step of providing a pair of securing ribs comprises providing chamfers on the pins.

18. A method according to claim 15 wherein the step providing the pins, securing ribs and ramps comprises the step of constructing at least one of the pins, securing ribs and ramps from a resilient material.

19. In combination, a biomedical electrode having an electrically conductive contacting tab, and a connector comprising:

fixed and movable jaws having tab engagement surfaces for engaging the contacting tab of the biomedical electrode, said fixed and movable jaws having proximal and distal ends, means for assembling the fixed and movable jaws in an assembled condition, and for mounting the jaws for relative pivotal movement between a) a tab accept position with the distal end of the movable jaw spaced from the distal end of the fixed jaw so that the tab of the biomedical electrode may be received between the jaws, and b) a closed position with distal ends of the fixed and movable jaws spaced more closely than in the tab accept position;

said means comprising one of said jaws having at least one pin and the other of said jaws having at least one recess for receiving the at least one pin;

biasing means for biasing the jaws toward the closed position;

at least one securing rib on one of said fixed and movable jaws for retaining the jaws in the assembled condition, and said at least one securing rib being receivable in the at least one recess.

20. A combination according to claim 19 wherein the fixed jaw is adapted to be connected to a leadwire, the fixed jaw having a pair of recesses for receiving the pins, said recesses comprising entry and locking portions; and further wherein the moveable jaw has two securing ribs thereon.

* * * * *